(12) United States Patent
Chavan et al.

(10) Patent No.: US 9,745,240 B2
(45) Date of Patent: Aug. 29, 2017

(54) METAL FREE PROCESS FOR ALLYLIC OXIDATION

(71) Applicant: COUNCIL OF SCIENTIFIC AND INDUSTRIAL RESEARCH, New Delhi (IN)

(72) Inventors: Subhash Prataprao Chavan, Maharashtra (IN); Pradeep Bhaskarrao Lasonkar, Maharashtra (IN)

(73) Assignee: COUNCIL OF SCIENTIFIC AND INDUSTRIAL RESEARCH, New Delhi (IN)

( * ) Notice: Subject to any disclaimer, the term of this patent is extended or adjusted under 35 U.S.C. 154(b) by 0 days.

(21) Appl. No.: 14/908,965

(22) PCT Filed: Jul. 28, 2014

(86) PCT No.: PCT/IN2014/000495
§ 371 (c)(1),
(2) Date: Jan. 29, 2016

(87) PCT Pub. No.: WO2015/015511
PCT Pub. Date: Feb. 5, 2015

(65) Prior Publication Data
US 2016/0159717 A1    Jun. 9, 2016

(30) Foreign Application Priority Data

Jul. 29, 2013 (IN) .......................... 2242/DEL/2013

(51) Int. Cl.
| | |
|---|---|
| C07C 45/39 | (2006.01) |
| C07C 45/64 | (2006.01) |
| C07C 37/06 | (2006.01) |
| C07C 45/34 | (2006.01) |

(52) U.S. Cl.
CPC .............. *C07C 45/34* (2013.01); *C07C 45/64* (2013.01); *C07C 2101/16* (2013.01)

(58) Field of Classification Search
CPC ................................. C07C 45/39; C07C 45/64
USPC ......................................... 568/317, 344, 802
See application file for complete search history.

(56) References Cited

PUBLICATIONS

Tong et al. "Highly efficient and metal-free oxidation of olefins by molecular oxygen under mild conditions". Tetrahedron, vol. 63, 2007, 7634-7639.*

* cited by examiner

*Primary Examiner* — Sikarl Witherspoon
(74) *Attorney, Agent, or Firm* — Margaret B. Brivanlou; Bryte V. Kelly; King & Spalding LLP

(57) ABSTRACT

The patent discloses a novel metal free process for the preparation of corresponding phenol and ketone via allylic oxidation of substituted cyclohexenes. Air is used as oxidant in the present process and can be used as such or optionally selected from pure oxygen or atmospheric oxygen. Moreover, the process of the present invention utilizes easily available starting materials and is a green eco-friendly, convenient and economical process with high yield of >60% and high selectivity.

15 Claims, No Drawings

METAL FREE PROCESS FOR ALLYLIC OXIDATION

FIELD OF THE INVENTION

The present invention lies in the field of synthetic chemistry and particularly relates to a novel metal free process for the preparation of corresponding phenol and ketone via allylic oxidation of substituted cyclohexenes.

BACKGROUND AND PRIOR ART

Oxidation is one of the most fundamental transformations in organic chemistry. Oxygenation of allylalkane or alkylarenes to the corresponding carbonyl compounds is an important reaction because an oxygen atom can be introduced into organic substrates. Conventionally, stoichiometric amount of an oxidant such as manganese dioxide, chromic acid, potassium dichromate, silver oxide, selenium dioxide and periodic acid have been employed, which suffer from the drawback that they produce environmentally unacceptable heavy metal wastes. An attractive option is the development of methods using molecular oxygen or air, especially from the perspective of atom efficiency and environmental concerns.

Recently, considerable progress has been made towards realizing the goal of using atmospheric oxygen for oxidation including Mukaiyama's oxidation-reduction-hydration reaction using several transition metal catalysts. Therefore, to improve yields, metal catalysts or photo-activation are employed to achieve the desired goal, but inviting environmental concerns.

Oxidative cleavage of the carbon-carbon double bond of substituted styrene derivatives to afford the corresponding ketones under an atmospheric pressure of molecular oxygen without the use of transition metal catalysts or photo-activation and oxidation of fluorine derivatives at the benzylic position to the corresponding carbonyl compounds using molecular oxygen promoted by activated carbon are reported in the literature.

So, a metal free oxidative process to obtain these vital constituent is an unaddressed need in the art, such that the process is not only green, but also results in the desired product in substantial yields.

Article titled, "Metal-Free Allylic Oxidation with Molecular Oxygen Catalyzed by g-C3N4 and N-Hydroxyphthalimide" by Guiyin Liu•Ruiren Tang•Zhen Wang in Catal Lett (2014) 144:717-722 reports a Polymeric graphitic carbon nitride (g-C3N4) is a layered graphite-like nitrogen-rich material (as a base), bearing the potential ability to reductively adsorb molecular oxygen for catalytic allylic oxidation. It provides a strategy for employing such nitride-rich g-C3N4 combined with NHPI to form an all organic metal-free composite and have examined its activity for allylic oxidation with molecular oxygen as the primary terminal oxidant. Furthermore, N-hydroxyphthalimide (NHPI) has been recognized as an efficient catalyst for aerobic oxidation of various organic compounds like cyclohexene under mild conditions (solvent is polar ex: acetonitrile) in the presence of various co-catalysts. It reports >74% conversion and >40% selectivity.

Article titled, "Allylic and benzylic oxidation reactions with sodium chlorite" by Samuel M. Silvestre, Jorge A. R. Salvador in Tetrahedron Volume 63, Issue 11, 12 Mar. 2007, Pages 2439-244 reports that various allylic and benzylic substrates were selectively oxidized to the corresponding enones in good yields using sodium chlorite, either in combination with tert-butyl hydroperoxide in stoichiometric conditions, or associated with N-hydroxyphthalimide as catalyst. These oxidation reactions were effectively and economically performed under mild, transition-metal free conditions and therefore the dual challenge of cost effectiveness and benign nature of the processes was met with.

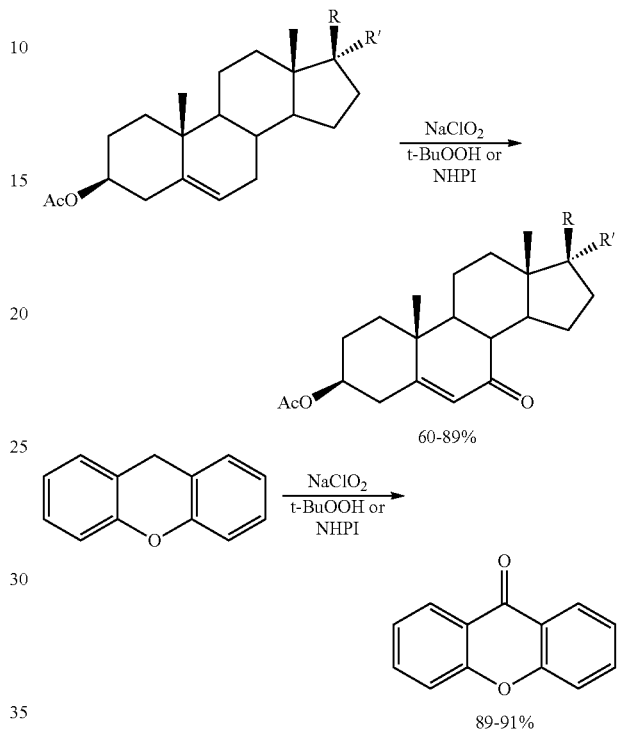

Article titled, "Highly efficient and metal-free oxidation of olefins by molecular oxygen under mild conditions" by Xinli Tong, Jie Xu in Tetrahedron Volume 63, Issue 32, 6 Aug. 2007, Pages 7634-7639 reports a Highly efficient and metal-free aerobic oxidations of cyclohexene and styrene performed under mild conditions in the presence of 1,4-diamino-2,3-dichloro-anthraquinone and N-hydroxyphthalimide. When cyclohexene was oxidized, an 89% conversion and 71% selectivity for 2-cyclohexen-1-one was obtained under 0.3 MPa at 80° C. for 5 h. Furthermore, more olefins were efficiently oxidized to corresponding oxygenated products under mild conditions.

Article titled, "Selective Allylic Oxidation of Cyclohexene Catalyzed by Nitrogen-Doped Carbon Nanotubes" by Yonghai Cao, Hao Yu, Feng Peng and Hongjuan Wang in ACS Catal., 2014, 4 (5), pp 1617-1625 reports Carbon nanotubes (CNTs) and nitrogen-doped CNTs (NCNTs) as metal-free catalysts in the selective allylic oxidation of cyclohexene using molecular oxygen as oxidant in the liquid phase. High cyclohexene conversion (up to 59.0%) and 620.1 mmol $g^{-1}$ $h^{-1}$ mass-normalized activities were obtained for NCNTs.

Article titled, "Copper-Catalyzed Allylic Oxidation of Cyclohexene with Molecular Oxygen" by Xu Zhang, Rong Yi, Tian Chen, Shichun Ni, Genlin Wang, Lei Yu in Scientific Journal of Frontier Chemical Development June 2013, Volume 3, Issue 2, PP. 25-29 reports a Copper-catalyzed aerobic allylic oxidation of cyclohexene under solvent-free conditions leads to 2-cyclohexenol and 2-cyclohexenone. This pathway is suitable for industrial production, owing to the high conversion rate and selectivity, the solvent-free conditions, the cheap catalyst and the environment-friendly oxidant and procedure.

Article titled, "Allylic Oxidation of Cyclohexene with Molecular Oxygen Using Cobalt Resinate as Catalyst" by Caixia Yin, Zehui Yang, Bin Li, Fengmei Zhang, Jiaqiang Wang, Encai Ou in Catalysis Letters 01/2009; 131(3):440-443 reports that Allylic oxidation of cychohexene under atmospheric pressure of molecular oxygen was carried out over cobalt resinate in the absence of solvent. It was shown that cobalt resinate exhibited promising catalytic activity for the oxidation of cyclohexene to 2-cyclohexen-1-ol and 2-cychohexen-1-one under mild condition.

Article titled, "Metal-free allylic/benzylic oxidation strategies with molecular oxygen: recent advances and future prospects" by Kexian Chen in *Green Chem.*, 2014, 16, 2344-2374 reports the selective oxo-functionalization of hydrocarbons under mild conditions with molecular oxygen as the terminal oxidant continues to be a hot topic in organic synthesis and industrial chemistry. This critical review summarizes recent significant advances achieved in this important field under the scope of green chemistry, which covers the promising applications and brief mechanistic profiles involving three kinds of efficient catalysts, namely N-hydroxyimides, homogeneous/heterogeneous light-sensitive molecules, and heteroatom-doped carbon materials, and concerns the sustainability of these methods.

Thus, there is a need in the art to provide processes for oxidation that effectively and efficiently employs atmospheric oxygen as an oxidant without affecting yield or desired product.

The process of the present invention overcomes several of the drawbacks of the prior art and provides an alternate to the processes which involved usage of unacceptable heavy metals or transition metals. The present process is green/eco-friendly, convenient, economical and offers other advantages like easily available starting materials, high yield and selectivity.

OBJECTIVE OF THE INVENTION

Main objective of the present invention is to provide to a metal free process for the preparation of corresponding phenol and ketone via allylic oxidation of substituted cyclohexenes.

Yet another object of the present invention is to provide to a metal free process for the preparation of corresponding phenol and ketone via allylic oxidation of substituted cyclohexenes with yield >60%.

SUMMARY OF THE INVENTION

Accordingly, the present invention provides a novel metal free process for the preparation of corresponding phenol and ketone via allylic oxidation of substituted cyclohexenes comprising the steps of
a. Mixing the substrate, solvent and base with continuous bubbling of air at 50 to 100° C. for 5 to 60 hours;
b. Extracting the product of step (a) and
c. purifying the product of step (b) to obtain the substantially pure desired product.

Abbreviations

Ph-Phenyl;
p-F-Ph-para fluro phenyl;
$^t$Bu-tert. Butyl;
CN-Cyano;

DETAILED DESCRIPTION OF THE INVENTION

In accordance with the objectives of the invention, the present invention provides a novel, environment friendly, convenient, economical metal free process for the preparation of corresponding phenol and ketone via allylic oxidation of substituted cyclohexenes with yield >60%.

In an embodiment, the present invention provides a novel metal free process for the preparation of phenol compound of formula I,

I

Wherein, R is selected from CHO, $COR_3$. $COOR_4$. COOH, CN, $NO_2$, Ts, Nitroethene, $\alpha,\beta$-unsaturated ketone, $\alpha,\beta$-unsaturated ester;
$R_1$ is selected from halides, particularly Cl, Br or I or phenyl or p-F-Ph;
$R_2$ is selected from H or alkyl, preferably methyl, tertiary butyl or phenyl;
$R_3$ is selected from alkyl, allyl or phenyl;
$R_4$ is selected from alkyl, allyl or benzyl;
, from substituted cyclohexene compound of formula III,

III

Wherein, R, $R_1$, $R_2$, $R_3$ and $R_4$ are as above;
Comprising:
a. Mixing the substrate, solvent and base with continuous bubbling of air at 50 to 100° C. for 5 to 60 hours; and
b. Extracting the product of step (a) and
c. purifying the product of step (b) to obtain the substantially pure desired product.

Yet another embodiment of the present invention is to provide to a metal free process for the preparation of corresponding phenol via allylic oxidation of substituted cyclohexenes with yield >60%.

The above process is shown below in Scheme 1:

Scheme: 1

III → I
Base, Polar solvent, Air, heat

In a preferred embodiment, the base for the process of the invention is selected from alkali carbonates, preferably Potassium carbonate and Cesium carbonate, 1,4-diazabicyclo[2.2.2]octane, 4-dimethylaminopyridine, 2,6-lutidine, triphenylphosphine, imidazole, triethylamine or pyridine.

In another preferred embodiment, the polar solvent of the invention is selected from water, alcohol-linear or branched selected from methanol or isopropyl alcohol, methyl cyanide or dimethyl formamide or degassed dimethyl formamide, either alone or in combination with tetra hydro furan.

In yet another preferred embodiment, the present invention provides a process wherein air is used as oxidant and can be used as such or optionally selected from pure oxygen or atmospheric oxygen.

In still another preferred embodiment the present invention provides a process wherein the temperature is preferably in the range of 70 to 90° C.; time is preferably in the range of 20 to 40 hours and yield is preferably >75%.

In an embodiment, the present invention provides a novel metal free process for the preparation of ketone compound of formula II,

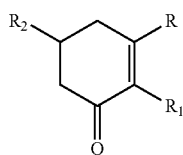

Wherein, R is selected from CHO, $COR_3$. $COOR_4$. COOH, CN, $NO_2$, Ts, Nitroethene, α,β-unsaturated ketone, α,β-unsaturated ester;

$R_1$ is selected from halides, particularly Cl, Br or I or phenyl or p-F-Ph;

$R_2$ is selected from H or alkyl, preferably methyl, tertiary butyl or phenyl;

$R_3$ is selected from alkyl, allyl or phenyl;

$R_4$ is selected from alkyl, allyl or benzyl;

, from substituted cyclohexene compound of formula III,

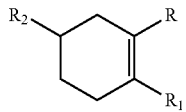

Wherein, R, $R_1$, $R_2$, $R_3$ and $R_4$ are as above;
comprising:
  a. Mixing the substrate and solvent with continuous bubbling of air at 50 to 100° C. for 5 to 60 hours and
  b. Extracting the product of step (a) and
  c. purifying the product of step (b) to obtain the substantially pure desired product.

Yet another embodiment of the present invention is to provide to a metal free process for the preparation of corresponding ketone via allylic oxidation of substituted cyclohexenes with yield >60%. The yield can sometimes go upto as high as or more than 89%.

The above process is shown below in Scheme 2:

Scheme: 2

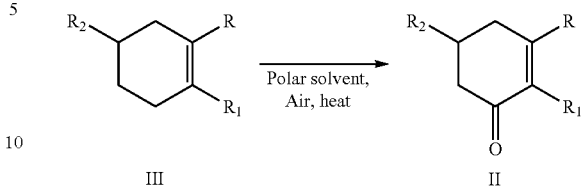

In yet another important embodiment, the extraction step involves filtering the product of step (a), as mentioned above; treating the filtrate with water; extracting with solvents such as EtOAc; washing the organic extracts with brine, dried (anhydrous $Na_2SO_4$), filtering the organic extract and removing the solvent in vacuo.

In yet another important embodiment, the purification is done preferably by column chromatography; most preferably flash column chromatography, although other alternates can also be used for purification.

In a preferred embodiment, the polar solvent of the invention is selected from water, alcohol-linear or branched selected from methanol or isopropyl alcohol, methyl cyanide or dimethyl formamide or degassed dimethyl formamide, either alone or in combination with tetra hydro furan.

In another preferred embodiment, the present invention provides a process wherein air is used as oxidant and can be used as such or optionally selected from pure oxygen or atmospheric oxygen.

In yet another preferred embodiment, the present invention provides a process wherein the temperature is preferably in the range of 70 to 90° C.; time is preferably in the range of 20 to 40 hours and yield is preferably >75%.

In an aspect the present invention provides a process for the synthesis of compound of formula I selected from the group comprising 3-hydroxybenzaldehyde; 3-Hydroxy-5-methylbenzaldehyde; 3-(tert-Butyl)-5-hydroxybenzaldehyde; 6-Hydroxy-[1,1'-biphenyl]-2-carbaldehyde; 4'-Fluoro-6-hydroxy-[1,1'-biphenyl]-2-carbaldehyde; (E)-4-(3-Hydroxyphenyl)but-3-en-2-one; (E)-3-(3-Hydroxyphenyl)-1-phenylprop-2-en-1-one; (E)-3-(3-Hydroxyphenyl)-1-(p-tolyl)prop-2-en-1-one; (E)-3-(3-Hydroxyphenyl)-1-(4-methoxyphenyl)prop-2-en-1-one; (E)-Ethyl 3-(3-hydroxyphenyl)acrylate; (E)-Ethyl 3-(3-hydroxy-5-methylphenyl)acrylate; (E)-Ethyl 3-(3-(tert-butyl)-5-hydroxyphenyl)acrylate. (Table: 1)

In another aspect the present invention provides a process for the synthesis of compound of formula II selected from the group comprising 2-Chloro-3-oxocyclohex-1-enecarbaldehyde, 6-Oxo-3,4,5,6-tetrahydro-[1,1'-biphenyl]-2-carbaldehyde. (Table: 1)

Table: 1 enlists the various exemplary embodiments of the process of the invention, wherein the starting substrates are prepared by well-known processes or reactions, and these starting material are readily available.

The invention will now be described in detail in connection with certain preferred and optional embodiments, so that various aspects thereof may be more fully understood and appreciated.

EXAMPLES

General Procedure

A mixture of cyclohexene (1 molar equiv) and $K_2CO_3$ (2 molar equiv) in DMF was placed in a two necked RB flask with continuous bubbling of air at 80° C. until the completion of reaction (TLC). The reaction mixture was filtered; the filtrate was then treated with water, extracted by EtOAc. The organic extracts were washed with brine, dried (anhydrous $Na_2SO_4$), filtered and the solvent removed in vacuo. The residue was purified by column chromatography (silica gel) using pet. ether/ethyl acetate as eluent. The yield was calculated, melting point determined and characterized by NMR.

Example 1

3-hydroxybenzaldehyde (2)

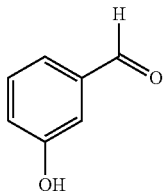

Cyclohexene 1 (200 mg, 1.39 mmol), and $K_2CO_3$ (383 mg, 2.78 mmol) in DMF (8 mL) was placed in a two necked RB flask with continuous bubbling of air at 80° C. for 12 h. Purification by flash column chromatography (silica gel, 9:1 pet. ether/ethyl acetate) afforded the brown solid compound 2 (mp.=100-103° C., 156 mg, 92% yield). $R_f$ 0.5 (20% Ethyl acetate/pet. ether).

$^1$H NMR (200 MHz, $CDCl_3$): δ 5.91 (s, 1H), 7.14 (dt, J=5.7, 2.8 Hz, 1H), 7.32-7.50 (m, 3H), 9.95 (s, 1H); $^{13}$C NMR (50 MHz, $CDCl_3+CCl_4+DMSO$): δ 115.1, 121.2, 121.9, 129.7, 137.5, 157.9, 191.9; GC-MS (EI): m/z=122 (M)$^+$.

Example 2

3-Hydroxy-5-methylbenzaldehyde (2a)

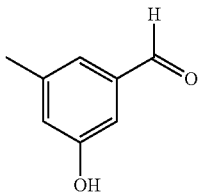

Cyclohexene 1a (0.2 g, 1.26 mmol), and $K_2CO_3$ (0.34 g, 2.53 mmol) in DMF (7 mL) was placed in a two necked RB flask with continuous bubbling of air at 80° C. for 20 h. Purification by flash column chromatography (silica gel, 7:3 pet. ether/ethyl acetate) afforded the brown solid compound 2a (mp.=78-80° C., 0.15 g, 89% yield). $R_f$ 0.5 (30% Ethyl acetate/pet. ether).

$^1$H NMR (200 MHz, $CDCl_3$): δ 2.39 (s, 3H), 6.22 (brs, 1H), 6.91-7.00 (m, 1H), 7.15-7.20 (m, 1H), 7.21-7.25 (m, 1H), 9.89 (s, 1H); $^{13}$C NMR (50 MHz, $CDCl_3+CCl_4+DMSO$): δ 20.7, 112.3, 121.6, 122.2, 137.2, 139.5, 157.6, 191.8; GC-MS (EI): m/z=136 (M)$^+$.

Example 3

3-(tert-Butyl)-5-hydroxybenzaldehyde (2b)

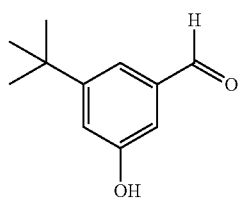

Cyclohexene 1b (200 mg, 1.00 mmol), and $K_2CO_3$ (276 mg, 2.00 mmol) in DMF (5 mL) was placed in a two necked RB flask with continuous bubbling of air at 80° C. for 24 h. Purification by flash column chromatography (silica gel, 8:2 pet. ether/ethyl acetate) afforded the red solid compound 2b (mp.=70-72° C., 137 mg, 77% yield). $R_f$ 0.5 (30% Ethyl acetate/pet. ether).

$^1$H NMR (200 MHz, $CDCl_3$): δ 1.36 (s, 9H), 7.17 (s, 1H), 7.21-7.29 (m, 2H), 7.48 (t, J=1.5 Hz, 1H), 9.94 (s, 1H); $^{13}$C NMR (50 MHz, $CDCl_3+CCl_4+DMSO$): δ 31.4 (3C), 35.0, 112.6, 120.0, 120.7, 137.6, 154.4, 156.9, 193.4; GC-MS (EI): m/z=178 (M)+.

Example 4

2-Chloro-3-oxocyclohex-1-enecarbaldehyde (3)

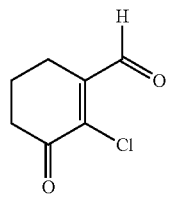

Cyclohexene 1 (200 mg, 1.39 mmol) in DMF (8 mL) was placed in a two necked RB flask with continuous bubbling of air at 80° C. for 12 h. Purification by flash column chromatography (silica gel, 9:1 pet. Ether/ethyl acetate) afforded the colorless liquid compound 3 (220 mg, 80% yield). $R_f$ 0.3 (10% Ethyl acetate/pet ether).

$^1$H NMR (200 MHz, $CDCl_3$): δ 1.97-2.20 (m, 2H), 2.53-2.77 (m, 4H), 10.44 (s, 1H); $^{13}$C NMR (50 MHz, $CDCl_3+CCl_4$): δ 20.9, 24.1, 38.4, 140.5, 145.6, 191.6, 192.1; GC-MS (EI): m/z=158 (M)$^+$, 130, 102, 95, 73, 65.

Example 5

6-Oxo-3,4,5,6-tetrahydro-[1,1'-biphenyl]-2-carbaldehyde (2e)

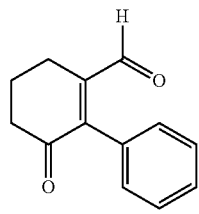

Cyclohexene 1e (200 mg, 1.07 mmol) in DMF (6 mL) was placed in a two necked RB flask with continuous bubbling of air at 80° C. for 17 h. Purification by flash column chromatography (silica gel, 9:1 pet. ether/ethyl acetate) afforded the yellow solid compound 2f (mp.=57-59° C., 158 mg, 72% yield). $R_f$ 0.6 (20% Ethyl acetate/pet. ether).

$^1$H NMR (400 MHz, CDCl$_3$): δ 2.08-2.23 (m, 2H), 2.67 (q, J=5.9 Hz, 4H), 7.18 (dd, J=6.7, 2.9 Hz, 2H), 7.42 (dd, J=4.9, 1.9 Hz, 3H), 9.69 (s, 1H); $^{13}$C NMR (100 MHz, CDCl$_3$+CCl$_4$): δ 21.6, 23.2, 39.0, 128.2 (2C), 129.3, 131.0, 131.1 (2C), 147.9, 148.1, 195.2, 200.2; HRMS (ESI) calculated for C$_{13}$H$_{13}$O$_2$, 201.0910 (M+H)$^+$. Found, 201.0908.

Example 6

6-Hydroxy-[1,1'-biphenyl]-2-carbaldehyde (2f)

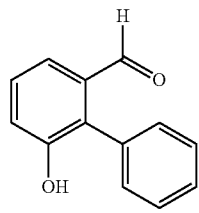

Cyclohexene 1e (200 mg, 1.07 mmol), and K$_2$CO$_3$ (296 mg, 2.15 mmol) in DMF (8 mL) was placed in a two necked RB flask with continuous bubbling of air at 80° C. for 22 h. Purification by flash column chromatography (silica gel, 8:2 pet. ether/ethyl acetate) afforded the green solid compound 2f (mp.=127-129° C., 159 mg, 75% yield). $R_f$ 0.4 (20% Ethyl acetate/pet. ether).

$^1$H NMR (200 MHz, CDCl$_3$+CCl$_4$): δ 5.21 (brs, 1H), 7.23 (dd, J=8.1, 1.3 Hz, 1H), 7.35-7.44 (m, 3H), 7.47-7.62 (m, 4H), 9.70 (s, 1H); $^{13}$C NMR (125 MHz, CDCl$_3$+CCl$_4$): δ 120.1, 121.1, 129.3, 129.4, 129.7 (2C), 131.0 (2C), 131.2, 131.8, 135.0, 153.5, 191.6; HRMS (ESI) calculated for C$_{13}$H$_{11}$O$_2$, 199.0754 (M+H)$^+$. Found, 199.0754.

Example 7

4'-Fluoro-6-hydroxy-[1,1'-biphenyl]-2-carbaldehyde (2g)

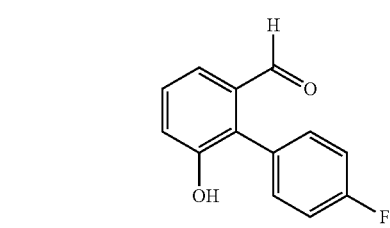

Cyclohexene 1g (200 mg, 1.02 mmol), and K$_2$CO$_3$ (281 mg, 2.04 mmol) in DMF (8 mL) was placed in a two necked RB flask with continuous bubbling of air at 80° C. for 24 h. Purification by flash column chromatography (silica gel, 8:2 pet. ether/ethyl acetate) afforded the orange solid compound 2g (mp.=128-130° C., 155 mg, 73% yield). $R_f$ 0.3 (20% ethyl acetate/pet. ether).

$^1$H NMR (500 MHz, CDCl$_3$+CCl$_4$): δ 7.24-7.31 (m, 4H), 7.37-7.42 (m, 2H), 7.43-7.46 (m, 1H), 7.61 (dd, J=7.7, 1.2 Hz, 1H), 9.74 (s, 1H); $^{13}$C NMR (125 MHz, CDCl$_3$+CCl$_4$): 116.6 (d, Ar—C, J$_{C-F}$=21.9 Hz, 2C), 120.4, 121.1, 127.5 (d, Ar—C, J$_{C-F}$=3.4 Hz), 129.4, 129.9, 132.6 (d, Ar—C, J$_{C-F}$=8.1 Hz, 2C), 135.1, 153.4, 163.7 (d, Ar—C, J$_{C-F}$=249.7 Hz), 191.3; HRMS (ESI) calculated for C$_{13}$H$_{10}$O$_2$F, 217.0659 (M+H)$^+$. Found, 217.1044.

Example 8

(E)-4-(3-Hydroxyphenyl)but-3-en-2-one (2h)

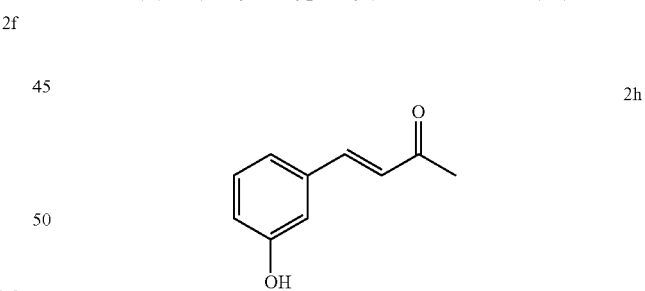

Cyclohexene 1h (200 mg, 1.08 mmol), and K$_2$CO$_3$ (298 mg, 2.16 mmol) in DMF (8 mL) was placed in a two necked RB flask with continuous bubbling of air at 80° C. for 32 h. Purification by flash column chromatography (silica gel, 8:2 pet. ether/ethyl acetate) afforded the white solid compound 2h (mp.=91-93° C., 144 mg, 82% yield). $R_f$ 0.3 (20% ethyl acetate/pet. ether).

$^1$H NMR (200 MHz, DMSO-d$_6$): δ 2.32 (s, 3H), 6.68 (d, J=16.4 Hz, 1H), 6.78-6.91 (m, 1H), 6.98-7.30 (m, 3H), 7.52 (d, J=16.4 Hz, 1H), 9.68 (s, 1H); $^{13}$C NMR (50 MHz, DMSO): δ 27.4, 114.7, 117.8, 119.5, 127.1, 130.0, 135.7, 143.5, 157.8, 198.2.

Example 9

(E)-3-(3-Hydroxyphenyl)-1-phenylprop-2-en-1-one (2i)

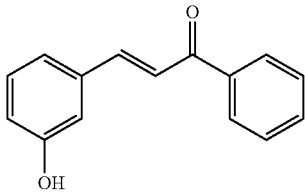

Cyclohexene 1i (200 mg, 0.81 mmol), and $K_2CO_3$ (223 mg, 1.62 mmol) in DMF (8 mL) was placed in a two necked RB flask with continuous bubbling of air at 80° C. for 23 h. Purification by flash column chromatography (silica gel, 8:2 pet. ether/ethyl acetate) afforded the light green solid compound 2i (mp.=150-152° C., 129 mg, 71% yield). $R_f$ 0.3 (20% ethyl acetate/pet. ether).

$^1$H NMR (400 MHz, $CDCl_3+CCl_4+DMSO$): δ 6.87-6.99 (m, 1H), 7.09-7.19 (m, 2H), 7.23 (d, J=7.9 Hz, 1H), 7.46-7.64 (m, 4H), 7.70 (d, J=15.6 Hz, 1H), 7.97-8.08 (m, 2H), 9.31 (s, 1H); $^{13}$C NMR (100 MHz, $CDCl_3+CCl_4+DMSO$): δ 114.2, 117.3, 118.9, 120.9, 127.5 (2C), 127.8 (2C), 129.0, 131.9, 135.1, 137.2, 144.1, 157.0, 189.2; HRMS (ESI) calculated for $C_{15}H_{13}O_2$, 225.0910 $(M+H)^+$. Found, 225.0907.

Example 10

(E)-3-(3-Hydroxyphenyl)-1-(p-tolyl)prop-2-en-1-one (2j)

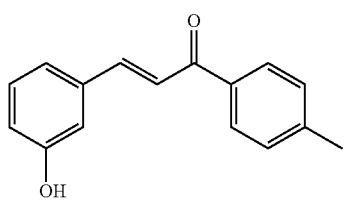

Cyclohexene 1j (200 mg, 0.76 mmol), and $K_2CO_3$ (212 mg, 1.53 mmol) in DMF (8 mL) was placed in a two necked RB flask with continuous bubbling of air at 80° C. for 30 h. Purification by flash column chromatography (silica gel, 8:2 pet. ether/ethyl acetate) afforded the yellow solid compound 2j (mp.=137-139° C., 120 mg, 66% yield). $R_f$ 0.3 (10% ethyl acetate/pet. ether).

$^1$H NMR (200 MHz, $CDCl_3+CCl_4+DMSO$): δ 2.24 (s, 3H), 6.56-6.78 (m, 1H), 6.86-6.94 (m, 2H), 6.96-7.14 (m, 3H), 7.27 (d, J=15.7 Hz, 1H), 7.48 (d, J=15.7 Hz, 1H), 7.60-7.82 (m, 2H), 8.87 (s, 1H); $^{13}$C NMR (125 MHz, $CDCl_3+CCl_4+DMSO$): δ 21.2, 114.5, 117.6, 119.3, 121.4, 128.1 (2C), 128.8 (2C), 129.4, 135.2, 135.6, 143.0, 144.2, 157.4, 189.2.

Example 11

(E)-3-(3-Hydroxyphenyl)-1-(4-methoxyphenyl)prop-2-en-1-one (2k)

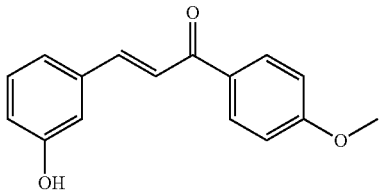

Cyclohexene 1k (200 mg, 0.72 mmol), and $K_2CO_3$ (200 mg, 1.45 mmol) in DMF (8 mL) was placed in a two necked RB flask with continuous bubbling of air at 80° C. for 32 h. Purification by flash column chromatography (silica gel, 8:2 pet. ether/ethyl acetate) afforded the yellow solid compound 2k (mp.=160-162° C., 112 mg, 61% yield). $R_f$ 0.3 (20% ethyl acetate/pet. ether).

$^1$H NMR (500 MHz, DMSO): δ 3.86 (s, 3H), 6.80-6.90 (m, 1H), 7.08 (d, J=8.9 Hz, 2H), 7.19-7.22 (m, 1H), 7.25 (t, J=7.7 Hz, 1H), 7.27-7.31 (m, 1H), 7.60 (d, J=15.6 Hz, 1H), 7.82 (d, J=15.6 Hz, 1H), 8.14 (d, J=8.9 Hz, 2H), 9.64 (s, 1H); $^{13}$C NMR (125 MHz, DMSO): δ 55.6, 114.1 (2C), 115.2, 117.7, 119.8, 121.9, 129.9, 130.5 (2C), 130.9, 136.1, 143.4, 157.7, 163.2, 187.5.

Example 12

(E)-Ethyl 3-(3-hydroxyphenyl)acrylate (2l)

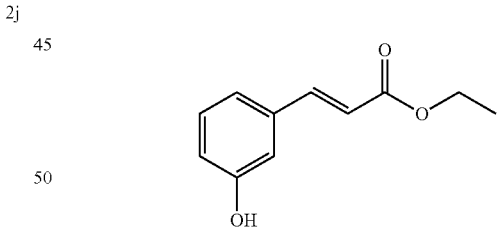

Cyclohexene 1l (200 mg, 0.93 mmol), and $K_2CO_3$ (200 mg, 1.87 mmol) in DMF (8 mL) was placed in a two necked RB flask with continuous bubbling of air at 80° C. for 36 h. Purification by flash column chromatography (silica gel, 9:1 pet. ether/ethyl acetate) afforded the yellow solid compound 2l (mp.=66-68° C., 145 mg, 81% yield). $R_f$ 0.4 (20% ethyl acetate/pet. ether).

$^1$H NMR (200 MHz $CDCl_3+CCl_4$): δ 1.34 (t, J=7.1 Hz, 3H), 4.27 (q, J=7.1 Hz, 2H), 6.38 (d, J=16.0 Hz, 1H), 6.83-6.95 (m, 1H), 6.97-7.11 (m, 2H), 7.14-7.42 (m, 1H), 7.62 (d, J=16.0 Hz, 1H); $^{13}$C NMR (50 MHz, $CDCl_3+CCl_4$): δ 14.4, 61.0, 114.8, 117.9, 118.1, 120.6, 130.2, 135.8, 145.3, 156.7, 167.9.

Example 13

(E)-Ethyl 3-(3-hydroxy-5-methylphenyl)acrylate (2m)

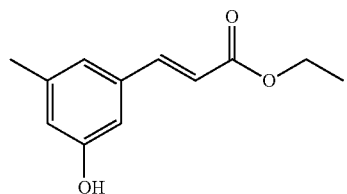

Cyclohexene 1m (200 mg, 0.88 mmol), and K$_2$CO$_3$ (242 mg, 1.75 mmol) in DMF (8 mL) was placed in a two necked RB flask with continuous bubbling of air at 80° C. for 48 h. Purification by flash column chromatography (silica gel, 9:1 pet. ether/ethyl acetate) afforded the yellow liquid compound 2m (128 mg, 71% yield). R$_f$ 0.5 (20% ethyl acetate/pet. ether).

$^1$H NMR (200 MHz, DMSO): δ 1.24 (t, J=7.1 Hz, 3H), 2.22 (s, 3H), 4.17 (q, J=7.1 Hz, 2H), 6.46 (d, J=16.0 Hz, 1H), 6.65 (s, 1H), 6.83 (s, 1H), 6.95 (s, 1H), 7.50 (d, J=16.0 Hz, 1H), 9.57 (s, 1H); $^{13}$C NMR (101 MHz, DMSO): δ 14.3, 21.0, 60.1, 112.0, 117.7, 118.4, 120.1, 135.0, 139.5, 144.8, 157.7, 166.3. HRMS (ESI) calculated for C$_{12}$H$_{15}$O$_3$, 207.1016 (M+H)$^+$. Found, 207.1015.

Example 14

(E)-Ethyl 3-(3-(tert-butyl)-5-hydroxyphenyl)acrylate (2n)

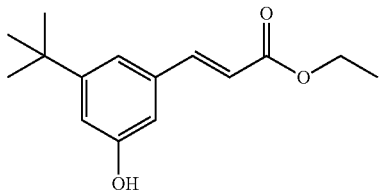

Cyclohexene 1n (200 mg, 0.88 mmol), and K$_2$CO$_3$ (242 mg, 1.75 mmol) in DMF (8 mL) was placed in a two necked RB flask with continuous bubbling of air at 80° C. for 40 h. Purification by flash column chromatography (silica gel, 9:1 pet. ether/ethyl acetate) afforded the yellow liquid compound 2n (128 mg, 78% yield).$^1$ R$_f$ 0.4 (20% ethyl acetate/pet. ether).

$^1$H NMR (200 MHz, CDCl$_3$+CCl$_4$) δ 1.28-1.41 (m, 12H), 4.27 (q, J=7.1 Hz, 2H), 6.38 (d, J=15.9 Hz, 1H), 6.82-6.88 (m, 1H), 6.88-6.94 (m, 1H), 7.08 (s, 1H), 7.63 (d, J=16.0 Hz, 1H). $^{13}$C NMR (50 MHz, CDCl$_3$+CCl$_4$): δ 14.6, 31.4 (3C), 34.9, 60.8, 111.6, 115.3, 118.2, 118.4, 135.6, 145.5, 153.9, 156.2, 167.4; HRMS (ESI) calculated for C$_{15}$H$_{21}$O$_3$, 249.1485 (M+H)$^+$. Found, 249.1481.

Advantages of Invention a. Easily available or easily synthesizable starting materials.
b. Green eco-friendly, convenient, economical process.
c. Avoids metal catalysts.
d. High yield and selectivity.

List of Tables:

TABLE 1

| Entry | substrate$^a$ | products | time (h) | yield (%)$^b$ |
|---|---|---|---|---|
| 1 | 1a | 2a | 20 | 89 |
| 2 | 1b | 2b | 24 | 77 |

TABLE 1-continued
| Entry | substrate[a] | products | time (h) | yield (%)[b] |
|---|---|---|---|---|
| 3 | 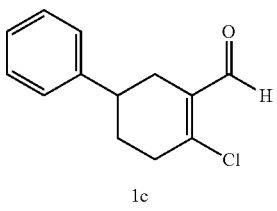 [SMILES: O=CC1=C(Cl)CCC(c2ccccc2)C1]<br>1c | 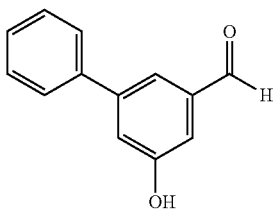<br>2c | 21 | 82 |
| 4 | 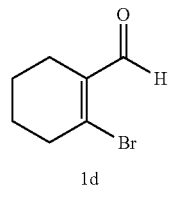<br>1d | 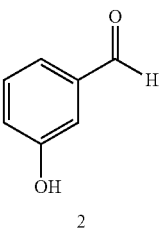<br>2 | 20 | 84 |
| 5 | 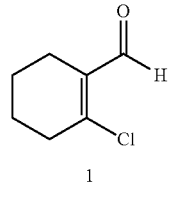<br>1 | 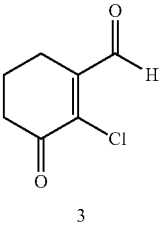<br>3 | 12 | 80 |
| 6 | 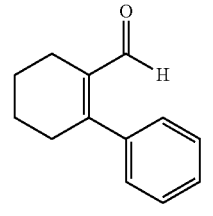<br>1e | 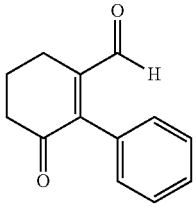<br>2e | 17 | 72 |
| 7 | 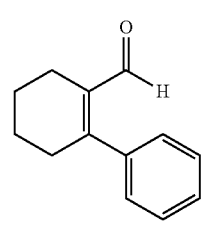<br>1e | 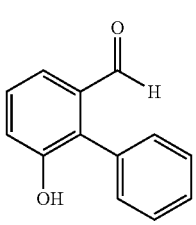<br>2f | 22 | 75 |
| 8 | 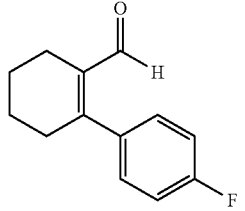<br>1g | 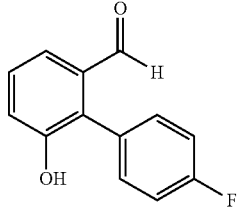<br>2g | 24 | 73 |

TABLE 1-continued
| Entry | substrate[a] | products | time (h) | yield (%)[b] |
|---|---|---|---|---|
| 9 | 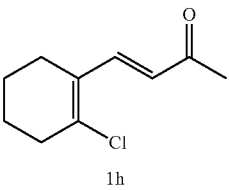 1h | 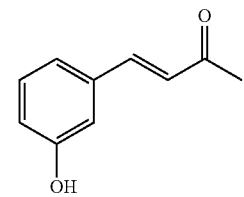 2h | 32 | 82 |
| 10 | 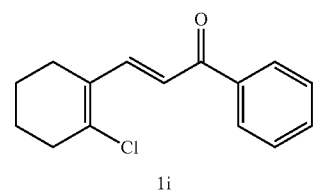 [SMILES: O=C(/C=C/C1=C(Cl)CCCC1)c1ccccc1] 1i | 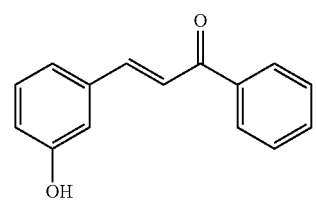 2i | 23 | 71 |
| 11 | 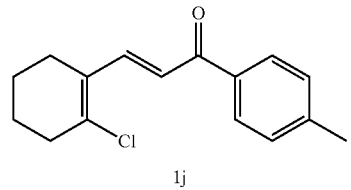 [SMILES: Cc1ccc(C(=O)/C=C/C2=C(Cl)CCCC2)cc1] 1j | 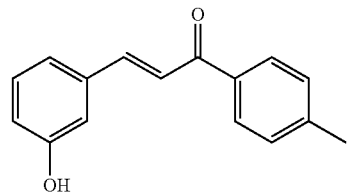 2j | 30 | 66 |
| 12 | 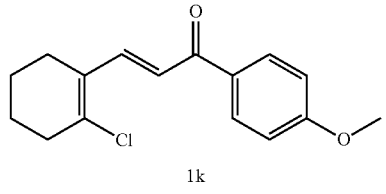 [SMILES: COc1ccc(C(=O)/C=C/C2=C(Cl)CCCC2)cc1] 1k | 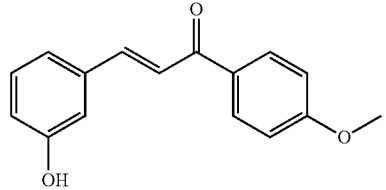 2k | 32 | 61 |
| 13 | 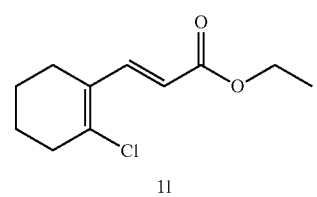 1l | 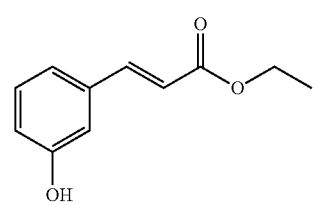 2l | 36 | 81 |
| 14 | 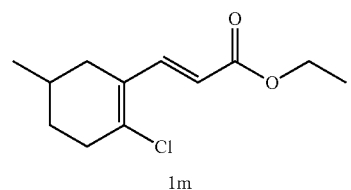 1m | 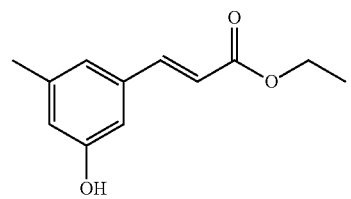 2m | 48 | 71 |

TABLE 1-continued

| Entry | substrate[a] | products | time (h) | yield (%)[b] |
|---|---|---|---|---|
| 15 | 1n | 2n | 40 | 78 |

The invention claimed is:

1. A metal free process for the synthesis of a phenol compound of Formula I or a ketone compound of Formula II,

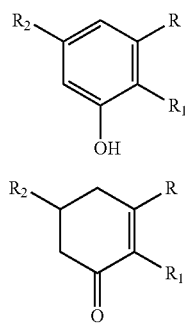

wherein, R is selected from CHO, $COR_3$, $COOR_4$, COOH, CN, $NO_2$, Ts, nitroethene, α,β unsaturated ketone, or α,β-unsaturated ester;
$R_1$ is selected from halides, phenyl or p-F-Ph;
$R_2$ is selected from H or alkyl;
$R_3$ is selected from alkyl, allyl or phenyl;
$R_4$ is selected from alkyl, allyl or benzyl;
the process comprising:
a. mixing a substituted cyclohexene of formula III

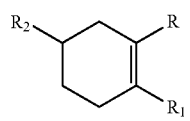

wherein, R, $R_1$, $R_2$, $R_3$ and $R_4$ are as above and a solvent, with continuous bubbling of molecular oxygen at 50 to 100° C. for 5 to 60 hours;
b. extracting the product of step (a); and
c. purifying the product of step (b) to obtain the phenol compound of Formula I or ketone compound of Formula II which is substantially purified.

2. The process according to claim 1, wherein the extraction step involves filtering the product of step (a); treating the filtrate with water; extracting with a solvent; washing the organic extract with brine; drying the organic extract with anhydrous $Na_2SO_4$; filtering the organic extract and removing the solvent in vacuo.

3. The process according to claim 1, wherein the purification is done by column chromatography.

4. The process according to claim 1, wherein the solvent is selected from water, methanol, isopropyl alcohol, methyl cyanide, dimethyl formamide or degassed dimethyl formamide, either alone or in combination with tetrahydrofuran.

5. The process according to claim 1, wherein the step (a) mixing a substituted cyclohexene of formula III and a solvent further comprises a base selected from alkali carbonates including Potassium carbonate and Cesium carbonate, 1,4-diazabicyclo[2.2.2]octane, 4-dimethylaminopyridine, 2,6-lutidine, triphenylphosphine, imidazole, triethylamine or pyridine.

6. The process according to claim 1, wherein the molecular oxygen is selected from pure oxygen or atmospheric oxygen.

7. The process according to claim 1, wherein the yield of phenol compound of Formula I or ketone compound of Formula II is greater than 60%.

8. The process according to claim 1, wherein the temperature is in the range of 70 to 90° C.; time is in the range of 20 to 40 hours and yield is greater than 75%.

9. The process according to claim 1, wherein the compound of Formula I is selected from the group consisting of 3-hydroxybenzaldehyde; 3-Hydroxy-5-methylbenzaldehyde; 3-(tert-Butyl)-5-hydroxybenzaldehyde; 6-Hydroxy-[1,1'-biphenyl]-2-carbaldehyde; 4'-Fluoro-6-hydroxy-[1,1'-biphenyl]-2-carbaldehyde; (E)-4-(3-Hydroxyphenyl)but-3-en-2-one; (E)-3-(3-Hydroxyphenyl)-1-phenylprop-2-en-1-one; (E)-3-(3-Hydroxyphenyl)-1-(p-tolyl)prop-2-en-1-one; (E)-3-(3-Hydroxyphenyl)-1-(4-methoxyphenyl)prop-2-en-1-one; (E)-Ethyl 3-(3-hydroxyphenyl)acrylate; (E)-Ethyl 3-(3-hydroxy-5-methylphenyl)acrylate; and (E)-Ethyl 3-(3-(tert-butyl)-5-hydroxyphenyl)acrylate.

10. The process according to claim 1, wherein the compound of Formula II is selected from the group consisting of 2-Chloro-3-oxocyclohex-1-enecarbaldehyde; and 6-Oxo-3,4,5,6-tetrahydro-[1,1'-biphenyl]-2-carbaldehyde.

11. The process according to claim 1, wherein $R_2$ is methyl, tertiary butyl or phenyl.

12. The process according to claim 2, wherein the extracting solvent is EtOAc.

13. The process according to claim 3, wherein the column chromatography is flash column chromatography.

14. The process according to claim 4, wherein the yield of phenol compound of Formula I or ketone compound of Formula II is greater than 60%.

15. The process according to claim 6, wherein the molecular oxygen is atmospheric oxygen.

* * * * *